(12) United States Patent
Bueschken et al.

(10) Patent No.: US 6,433,230 B1
(45) Date of Patent: Aug. 13, 2002

(54) PROCESS FOR CONDUCTING AN ALDOL CONDENSATION

(75) Inventors: Wilfried Bueschken; Klaus-Diether Wiese, both of Haltern; Guido Protzmann, Marl, all of (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 09/716,941

(22) Filed: Nov. 22, 2000

(30) Foreign Application Priority Data

Nov. 24, 1999 (DE) .......................................... 199 56 410

(51) Int. Cl.$^7$ ............................................ C07C 49/203
(52) U.S. Cl. ...................... 568/388; 568/312; 568/313; 568/343; 568/345; 568/347; 568/353; 568/390; 568/391; 568/433; 568/458; 568/461; 568/463; 568/464
(58) Field of Search ................................ 568/312, 313, 568/343, 345, 353, 388, 390, 391, 433, 458, 461, 463, 464, 347

(56) References Cited

FOREIGN PATENT DOCUMENTS

| DE | 35 30 839 | 3/1987 |
|----|-----------|--------|
| DE | 42 43 524 | 6/1994 |
| EP | 0 562 450 | 9/1993 |
| EP | 0 646 563 | 4/1995 |
| WO | WO 93/20034 | 10/1993 |

OTHER PUBLICATIONS

Yu–Ren Chin et al, Process Economics Program Report No. 21C, "Oxo Alcohols", *SRI International*, Apr. 1986, pp. 2.

*Primary Examiner*—Sreeni Padmanabhan
(74) *Attorney, Agent, or Firm*—Oblon, Spivak, McClelland, Maier & Neustadt, P.C.

(57) ABSTRACT

α,β-Unsaturated keto compounds are prepared by base-catalyzed aldol condensation of aldehydes and/or ketones having from 1 to 15 carbon atoms, comprising:

reacting the aldehydes and/or ketones with an aqueous catalyst solution under adiabatic reaction conditions; and separating the reaction mixture obtained by rapid distillation into a top product comprising water, aldehyde and/or ketone and a bottom product comprising α,β-unsaturated keto compounds and aqueous catalyst phase.

18 Claims, 2 Drawing Sheets

PROCESS FOR CONDUCTING AN ALDOL CONDENSATION

BACKGROUND OF THE INVENTION

1. Field of the Invention

The present invention relates to a process for conducting aldol condensation reactions and to the use of the aldol condensation products.

2. Description of the Background

Aldol condensations are important reactions which are conducted on an industrial scale. The α,β-unsaturated carbonyl compounds obtained from them are, because of their reactivity, starting materials for the synthesis of many organic compounds such as, for example, intermediates for the production of fragrances or pharmaceuticals. In addition, α,β-unsaturated aldehydes can be hydrogenated to form saturated aldehydes which can, inter alia, be oxidized to the corresponding carboxylic acids. These acids can be used for producing lubricants, desiccants, peresters or stabilizers for plastics. Complete hydrogenation of α,β-unsaturated aldehydes gives saturated primary alcohols which are employed for producing detergents and plasticizers or as solvents.

The aldol condensation is the reaction of two keto compounds (aldehyde or ketone) with elimination of water to form a compound which contains both an olefinic double bond and a carbonyl function. If, for example, only one aldehyde is used as starting material, an unsaturated aldehyde having twice the number of carbon atoms as the starting aldehyde is formed. This type of reaction is catalyzed by acids and bases. In industrial processes, preference is given to bases, especially inorganic bases such as NaOH.

By far the most important industrial process of this type is the condensation of n-butyraldehyde to form 2-ethylhex-2-enal, which is an intermediate for the preparation of 2-ethylhexanol, a plasticizer alcohol.

A possible way of conducting this reaction is described in the SRI-Report 21 C. The reaction is conducted in two condensation reactors connected in series. As catalyst, use is made of a two percent strength sodium hydroxide solution. The residence time in each of the two reactors is about 14 minutes. The reaction temperature is maintained at 85° C. in the first reactor and 90° C. in the second reactor by cooling, i.e. the reaction is not adiabatic and the heat of reaction has to be removed. The reaction mixture is subsequently separated into an aqueous catalyst solution and an organic phase by phase separation in a settling vessel. The catalyst phase is returned to the first reactor. Part of the catalyst is bled off to remove by-products and water of reaction and is replaced by fresh catalyst solution. The organic product phase which has been separated is washed free of base using water. The wash water is pumped to the first reactor. Water and n-butyraldehyde are separated from the crude product by distillation and are recirculated to the first reactor. The product which has been freed of these low boilers can be used as such or can be worked-up by distillation to give the pure product (2-ethylhex-2-enal).

As disclosed in DE 3530839, the condensation of n-butyraldehyde to form 2-ethylhex-2-enal is conducted in a flow tube at temperatures of 100–170° C. under superatmospheric pressure in the presence of 0.5–5% strength sodium hydroxide solution as catalyst. The residence time is 0.2–5 minutes. After cooling to 60° C., the reaction product is separated into the catalyst phase and product phase by phase separation. Part of the catalyst phase is bled off and replaced by fresh catalyst solution and the catalyst phase is then recirculated to the flow tube.

A disadvantage of the process is that water of reaction is removed by the discharge of catalyst solution. This stream is thus significantly larger than that which would be necessary purely for removing the carboxylic acids formed by the Cannizzaro reaction. This removal, therefore, results in a high catalyst consumption. The sodium hydroxide solution discharged contains organic compounds and, therefore, has to be worked-up or disposed of in an effluent treatment plant, thus incurring additional costs.

Decenal, a precursor for the plasticizer alcohol decanol (main constituent: isopropylheptanol), is prepared analogously to 2-ethylhexenal by aldol condensation of $C_5$-aldehydes. Various processes for achieving this are described, for example, in DE 4 243 524, EP 562 450, EP 562 451, EP 646 563 and DE 4 243 524.

According to the disclosures of EP 562 451 and EP 646 563, the aldol condensation of valeraldehyde is conducted in a conventional manner, i.e. using a method analogous to the preparation of 2-ethylhex-2-enal described in SRI 21 C. It, therefore, suffers from the same disadvantages.

Another continuous aldol condensation process is disclosed in EP 634 994. This process comprises the following steps:

a) The starting aldehyde and the aqueous catalyst solution are fed into a stirred reactor operated under nonadiabatic conditions.

b) The reaction mixture obtained from the stirred reactor is introduced into the middle section of a distillation column.

c) The product obtained at the top of the distillation column is a gaseous mixture of starting material and water which, after condensation, separates into an upper organic phase and a lower aqueous phase.

d) Part of the aqueous phase is discharged.

e) The organic upper phase is recirculated to the reactor.

f) The bottom product obtained in the distillation is a mixture containing the aqueous catalyst solution, product and by-products (higher aldol addition or aldol condensation products, carboxylic acids and alcohols formed by the Cannizzaro reaction).

g) The bottom product is cooled.

h) The cooled bottom product separates into two phases. The upper organic phase contains the product, relatively high molecular weight products of further reactions and small amounts of catalyst solution. The lower phase comprises the aqueous catalyst solution which contains the carboxylic acid formed as by-product as salt and is saturated with product.

i) The catalyst phase which has been separated is recirculated to the reactor.

h) The product phase (upper phase) is taken off.

This process has a number of disadvantages:

a) The energy balance is capable of improvement, since the heat of reaction is not utilized. The heat of reaction has to be controlled by cooling the reactor, and the distillation of the reactor output requires energy. A cooling medium is needed to cool the bottom product obtained from the distillation.

b) During the distillation, the reaction mixture, which is basic because of the presence of the catalyst phase, is subject to thermal stress, which favors the formation of byproducts by the Cannizzaro reaction and thus reduces the yield. As a result, a larger amount of catalyst solution has to be bled off and replaced by fresh solution in order to keep the concentration of carboxylic acid salts constant.

c) The crude end product is taken from the plant without washing. It, therefore, still contains small amounts of catalyst, which constitutes a loss of catalyst. Furthermore, the entrained catalyst can cause deterioration of product quality during storage of the crude product. When using the product in a chemical synthesis, e.g. a hydrogenation, these catalyst residues can cause problems.

A need, therefore, continues to exist for an aldol condensation reaction which is industrially more acceptable for the product of condensation product.

SUMMARY OF THE INVENTION

Accordingly, one object of the invention is to provide a process for the condensation of keto compounds by the aldol condensation reaction to form α,β-unsaturated keto compounds which is more environmentally friendly and has better economics than the known processes.

Briefly, this object and other objects of the present invention as hereinafter will become more readily apparent can be attained by a process for preparing α,β-unsaturated keto compounds by base-catalyzed aldol condensation of aldehydes and/or ketones having from 1 to 15 carbon atoms, comprising:

reacting the aldehydes and/or ketones with an aqueous catalyst solution under adiabatic reaction conditions; and separating the reaction mixture obtained by rapid distillation into a top product comprising water, aldehyde and/or ketone and a bottom product comprising α,β-unsaturated keto compounds and aqueous catalyst phase.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
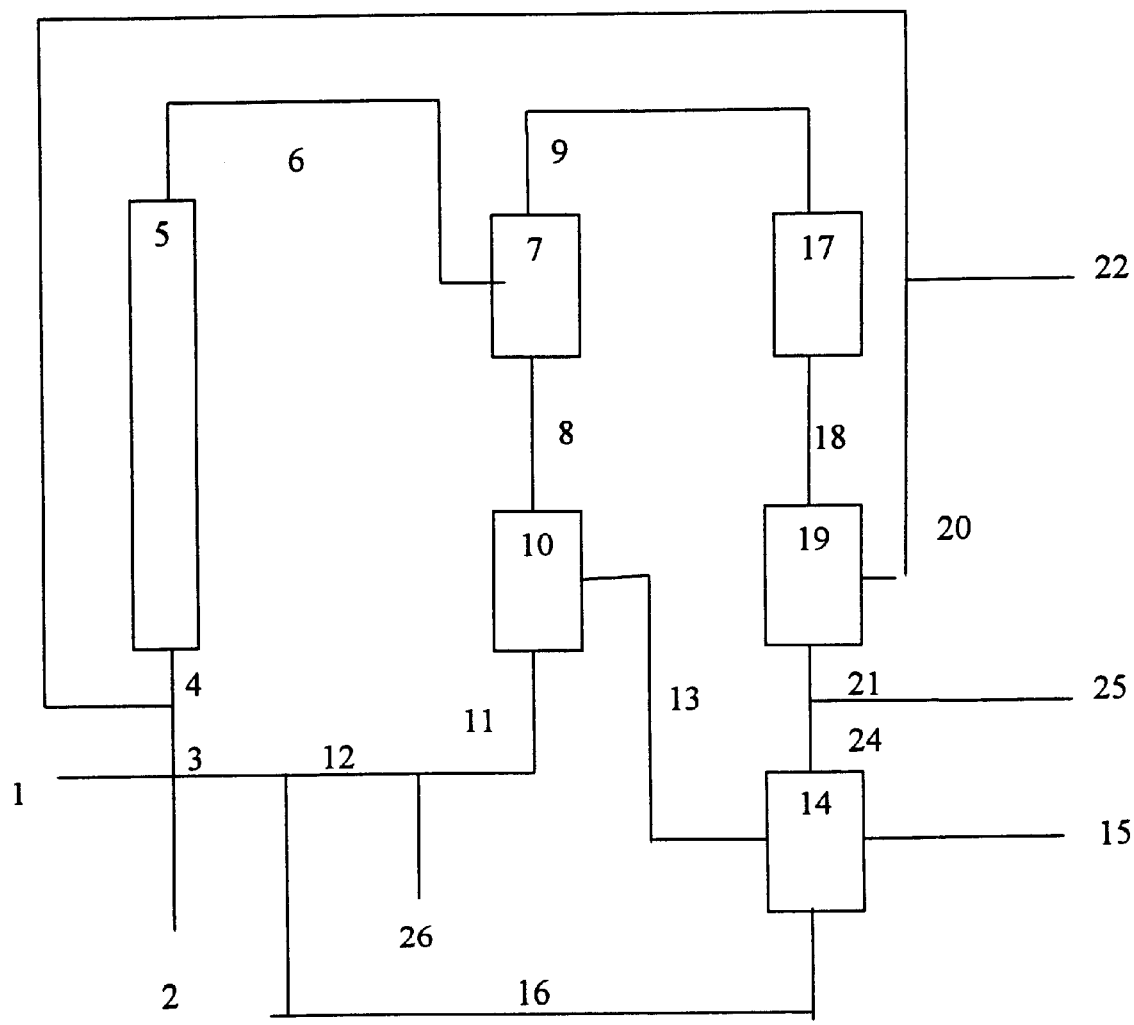
FIG. 1 is a process flow scheme for conducting the aldol condensation reaction of the invention.

The present invention provides a process for preparing α,β-unsaturated keto compounds by base-catalyzed aldol condensation of aldehydes and/or ketones having from 1 to 15 carbon atoms, wherein the aldehydes and/or ketones are reacted with an aqueous catalyst solution under adiabatic conditions and the reaction mixture obtained is separated by rapid distillation into a top product comprising water, aldehyde and/or ketone and a bottom product comprising α,β-unsaturated keto compounds and aqueous catalyst phase.

The process of the invention is suitable for the reaction of all keto compounds or mixtures of keto compounds which can undergo aldol condensation reactions. If only one keto compound is used, the compound has to have two α-hydrogens (vicinal to the CO group) on the same carbon atom. If two or more different keto compounds are used, at least one of the compounds has to have two α-hydrogens on the same carbon atom.

The following compounds are particularly suitable as starting materials for the process of the invention and are keto compounds having two α-hydrogens on the same carbon atom such as acetaldehyde, propanal, n-butyraldehyde, n-valeraldehyde, 3-methylbutyraldehyde, n-hexanal, 3-methylpentanal, 4-methylpentanal, n-heptanal, n-octanal, n-nonanal, n-decanal, acetone, methyl ethyl ketone, cyclohexanone and acetophenone.

Suitable examples of keto compounds having an α-hydrogen on the same carbon atom include isobutyraldehyde, 2-methylbutyraldehyde, 2-methylpentanal, 2-ethylhexanal, cyclohexyl carbaldehyde and phenyl-2-propyl ketone.

Suitable examples of keto compounds having no α-hydrogen atoms include benzaldehyde, 2,2-dimethylpropanal and benzophenone.

Preferred keto compounds include those having from 1 to 15 carbon atoms and/or mixtures thereof. Aldehydes used are, in particular, those which have been produced by hydroformylation of olefins. Preferred starting materials include n-butyraldehyde, n-valeraldehyde, a mixture of n-butyraldehyde and isobutyraldehyde, mixtures of n-valeraldehyde with 2-methylbutyraldehyde and 3-methylbutyraldehyde and the corresponding three-component mixture. It is likewise possible to use a mixture of $C_4$- and $C_5$-aldehydes or a mixture of the isomeric nonanals.

As to the catalyst, it is possible to use hydroxides, hydrogen carbonates, carbonates, carboxylates or their mixtures in the form of their alkali metal or alkaline earth metal compounds or tertiary amines, in each case as aqueous solutions. Preferred catalysts include alkali metal hydroxide solutions such as sodium hydroxide solution.

The concentration of the basic catalyst in the aqueous catalyst solution generally ranges from 0.1 to 10% by weight, in particular from 0.1 to 3% by weight. Since water is formed in the reaction, the concentration of the catalyst solution in the feed to the reactor is higher than in the outflow from the reactor. Because of the Cannizzaro reaction, which occurs as a secondary reaction, alcohols and carboxylic acids are formed from the starting material and, to a lesser extent, from the product, and these compounds accumulate in the catalyst phase in the form of their salts. Bleeding off part of the catalyst solution and replacing it with an equivalent amount of fresh alkali enables the concentration of the carboxylic acid salts in the aqueous catalyst solution to be kept in the range from 5 to 40% by weight.

The proportion of aqueous catalyst solution relative to the organic starting material phase can vary within wide limits. If a tube reactor is used in the process of the invention, weight ratios of organic to catalyst phase of at least 1:2, preferably greater than 1:10, are useful. The same applies to the use of stirred vessels.

In specific embodiments of the present invention, the concentration of the catalyst solution is controlled by bleeding or recirculation measures.

The temperature of the reaction mixture at the outlet from the reactor is advantageously above the boiling point of the aqueous catalyst solution ranging from 80° C. to 180° C. When using a stirred vessel, this temperature corresponds to the temperature of the reaction mixture. In a flow tube or tube reactor, this temperature is reached only at the end of the reactor because of the adiabatic reaction conditions. Regardless of the type of reactor, the process of the invention is conducted adiabatically.

The pressure in the reaction apparatus is determined by the vapor pressures of the components in the reaction mixture at the prevailing temperatures. The aldol condensation of the invention is preferably conducted at a pressure of 1.1 to 20 bar.

The reaction apparatus for the aldol condensation of the invention can be at least one stirred vessel or a cascade of stirred vessels or at least one tube reactor or flow tube. In each type of reactor, intensive mixing of the two phases can be ensured by means of stirring devices or static mixers.

The starting material(s) is/are fed into the adiabatically operated reactor either together with or separately from the aqueous catalyst solution, if desired together with the top product from the rapid distillation step.

The reaction mixture leaving the reactor is depressurized, preferably to atmospheric pressure, in a rapid distillation apparatus. In the case of high-boiling starting materials, depressurization can be conducted under a slight vacuum of 0.1–1 bar.

The rapid distillation can be conducted as a flash distillation, as a distillation in a falling film evaporator, as a distillation in a thin film evaporator or as a distillation in a combined falling film/thin film evaporator. The flash distillation described below is the preferred technique, because it is the simplest technically. The rapid distillation should subject the reaction product to as little as possible thermal and chemical stress because of the catalyst and is, therefore, preferably conducted using residence times of not more than one minute. Comparable distillations have residence times of over 5 minutes. The brief distillation, in particular the flash distillation, is preferably conducted adiabatically, as a result of which the temperature of the bottom product is lower than that of the feed.

The reaction mixture is separated by the rapid distillation into a top product comprising water, aldehyde and/or ketone (starting material) and a bottom product comprising $\alpha,\beta$-unsaturated keto compounds and aqueous catalyst phase.

The top product may contain, in addition to the above-mentioned mixture of water and starting material, other low boilers, e.g. the alcohol corresponding to the starting material, and small amounts of $\alpha,\beta$-unsaturated keto compounds. The bottom product may contain, in addition to the mixture of $\alpha,\beta$-unsaturated keto compounds and catalyst phase, higher condensation products, products from the Cannizaro reaction of the starting materials and small amounts of starting materials.

The preferably uncooled bottom product from the rapid distillation can be separated in a settling vessel into an organic phase (product phase) and an aqueous phase, i.e. the aqueous catalyst phase.

The organic product phase, after removing traces of catalyst by washing with water, preferably using the aqueous phase of the top product of the rapid distillation, is withdrawn from the process. This crude product can be used directly for other reactions, e.g. hydrogenations. If desired, high boilers (higher aldol addition and aldol concentration products) can additionally be separated and at least partly returned to the condensation reactor.

The aqueous catalyst phase is returned to the aldol condensation reaction, if desired together with the wash water obtained,. To keep the by-product level constant, a small part of the catalyst phase can be bled off and replaced by an equivalent amount of fresh catalyst.

The top product from the rapid distillation is condensed at a temperature which is both below the boiling point of water and below that of a minimum azeotrope. This gives a liquid mixture which can be separated into an organic phase and an aqueous phase.

The organic phase of the top product is, if desired, pumped back into the aldol condensation reactor while a portion of the organic phase may be bled off.

Part of the aqueous lower phase can, for example, be used for washing the product phase, as has already been mentioned above.

The other part of the aqueous phase of the top product or the total aqueous phase serves to discharge the water of reaction. The aqueous phase still contains organic substances, primarily starting material, in dissolved form. The wastewater can be passed directly or after preliminary purification to the effluent treatment plant. The preliminary purification can be conducted by means of steam stripping or by azeotropically removing organic substances by distillation.

The aldol condensation products prepared by the process of the invention can, after hydrogenation to give the unsaturated alcohols, be used, in particular, as detergents or plasticizer alcohol.

The aldol condensation process of the invention is preferably conducted continuously. FIG. 1 shows, by way of example, a block diagram of a plant in which the process of the invention can be conducted.

A mixture 4 comprising starting material 1, if desired, recirculated organic phase 23, aqueous catalyst solution 2, recirculated catalyst solution 12 and washing water 16 is fed into the reactor 5. The reaction mixture 6 leaving the reactor is depressurized in the rapid distillation apparatus, which is a flash vessel 7. This gives a top product 9 and a bottom product 8. The bottom product 8 is separated in the settling vessel 10 into the product phase 13 and the catalyst phase 11 which is recirculated to the reactor 5, if desired after bleeding off a substream 26. The product phase 13 is washed in the scrubber 14 using water 24 from the settling vessel 19. The product phase 15 leaves the plant. The wash water 16 is recirculated to the reactor 5. The gaseous top product 9 is condensed in the cooler 17. The condensate 18 is separated in the settling vessel 19 into an organic phase 20 and an aqueous phase 21. The organic phase 20 is, after bleeding off a substream 22, conveyed as stream 23 to the reactor 5. The water of reaction 25 is removed from the aqueous phase 21 and the remainder 24 is used for washing the product phase in the vessel 14.

The process of the invention has notable advantages over processes known in the literature. That is, as a result of the adiabatic reaction conditions, the heat of reaction remains in the reaction mixture. This heat is utilized in the rapid distillation to vaporize the top product, i.e. water and unreacted starting material. The heat losses from the process are also minimized by the stream 8 being able to be separated in the vessel 10 without cooling and the catalyst phase 11 being able to be returned hot to the reactor.

Compared to the process described in EP 0 634 994 B1, the process of the invention additionally has the following advantages. One advantage of the process is that since remains in the vessels 7 and 10 for only a short time, the reaction mixture is subject to thermal and chemical stresses in the presence of the alkaline catalyst solution for a significantly shorter time than in a fractional distillation. As a result, a smaller amount of carboxylic acid is formed by the Cannizzaro reaction. This means a higher yield of product. Since less carboxylic acid, which is present as salt in the catalyst solution, has to be discharged, the catalyst loss is smaller. Furthermore, it is advantageous to utilize part of the water which is removed by distillation to wash the crude product.

Compared to conventional processes in which the water of reaction remains in the catalyst solution and is discharged together with it, the process of the invention has the additional advantage of a lower catalyst consumption.

Having now generally described this invention, a further understanding can be obtained by reference to certain specific Examples which are provided herein for purposes of illustration only and are not intended to be limiting unless otherwise specified.

Figure 2:
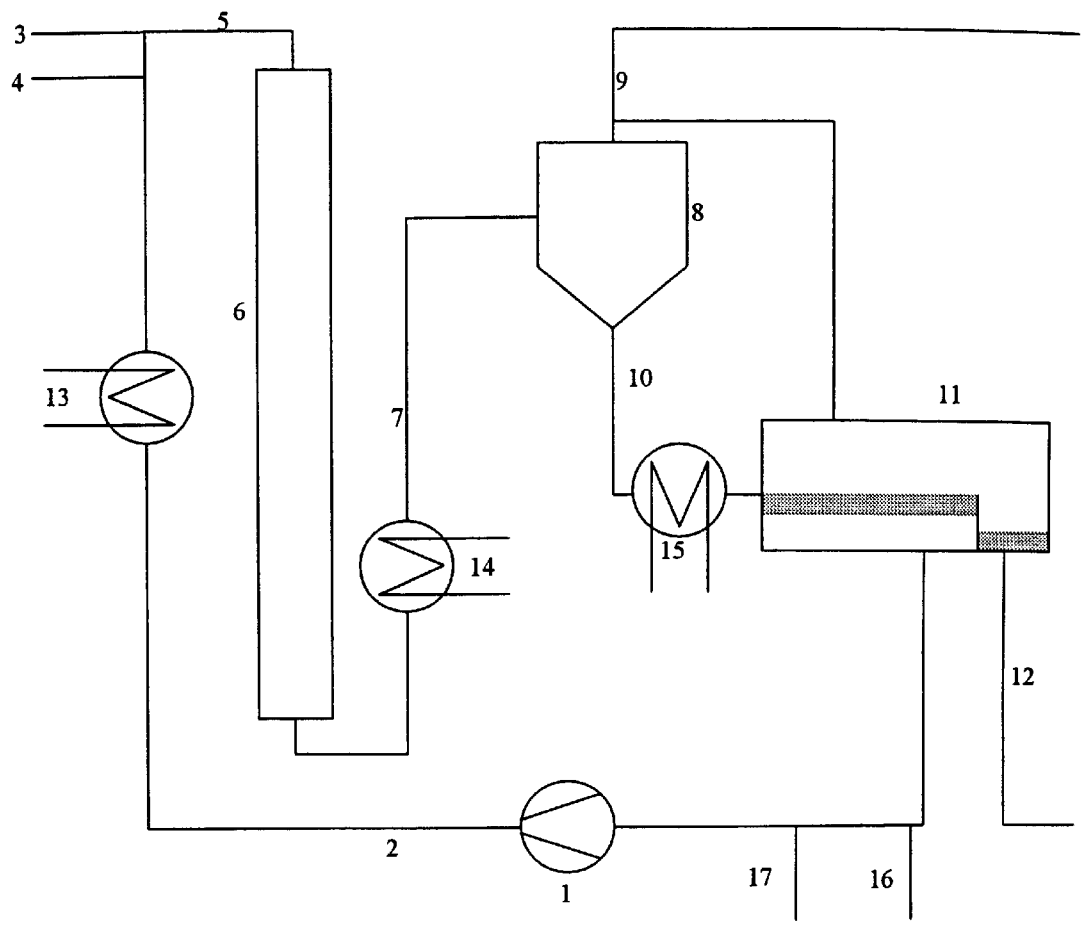
FIG. 2 depicts the process scheme by which the data of the examples were obtained.

The aldol condensation is conducted in an experimental apparatus shown schematically in FIG. 2. In this apparatus, the catalyst phase 2 is circulated by means of a pump 1. An aldehyde or the aldehyde mixture is introduced into a tube reactor 6 through line 3, or different aldehydes are introduced separately through lines 3 and 4 into the tube reactor, and mixed into the catalyst. For the Examples described below, pentanal as starting material was mixed in exclusively via line 3. The multiphase mixture 5 obtained this way is pumped through the tube reactor 6 having a length of 3 m and a diameter of 17.3 mm which is provided with static mixing elements having a hydraulic diameter of 2 mm. The resulting mixture 7, comprising the reaction product, unreacted starting material and the catalyst phase, is depressurized in the flash vessel 8. This gives a top product 9 and a bottom product 10. The liquid stream 10 is passed to a phase separation vessel 11. Here, the aqueous catalyst phase 2 is separated and recirculated. The organic phase which has run over a weir contains the reaction product and is removed via line 12. The reactor 6 is operated under nitrogen at about 2 bar; the pressure of the flash vessel 8 is shown in Table 1.

To ensure a constant catalyst composition, a small substream of the catalyst is bled off via line 16 and replaced by introduction of fresh catalyst via line 17.

The heat exchangers 13, 14 and 15 located outside the reactor are optional. The reaction itself or the reactor 6 are operated adiabatically. The heat exchanger 13 can be employed for preheating the catalyst phase, particularly when starting up the reactor. The heat exchanger 14 can be used to remove a portion of the heat of reaction, e.g. if the reaction mixture is too hot for the rapid distillation. The heat exchanger 15 serves to control the phase separation of the bottom product, since this is temperature-dependent.

The following Examples describe the use of the above-described continuous apparatus for the process of the invention, using the aldol condensation of pentanal to form 2-propylheptenal (2PHal) as an example. A 400 kg/h amount of catalyst were passed through the reactor at the autogenous pressure of the reactants. The temperature of the catalyst, the pressure in the flash vessel and the feed rate of starting material (3) are shown in Table 1. Table 2 describes the top and bottom products from the flash vessel.

The catalyst solution used was aqueous sodium hydroxide solution having a concentration of 3% by weight of NaOH.

TABLE 1

| Example | Pentanal (3) [g/h] | p (flash) [bar] | T [° C.] |
|---------|--------------------|-----------------|----------|
| 1 | 1150 | 0.80 | 110 |
| 2 | 6200 | 0.70 | 110 |
| 3 | 13000 | 0.50 | 110 |
| 4 | 1100 | 0.55 | 105 |
| 5 | 4900 | 0.45 | 105 |
| 6 | 7900 | 0.36 | 105 |
| 7 | 1050 | 0.20 | 98 |
| 8 | 4900 | 0.15 | 98 |

TABLE 2

| | Top product (9) | | | Bottom product (10) | |
|---|---|---|---|---|---|
| Example | Water [g/h] | Pentanal [g/h] | 2PHal [g/h] | 2PHal [g/h] | Pentanal [g/h] |
| 1 | 109 | 88 | 26 | 940 | 0.9 |
| 2 | 594 | 433 | 101 | 5108 | 4.3 |
| 3 | 1293 | 614 | 276 | 11116 | 6.1 |
| 4 | 97 | 150 | 21 | 838 | 1.5 |
| 5 | 451 | 498 | 98 | 3878 | 5.0 |
| 6 | 777 | 409 | 167 | 6679 | 4.1 |
| 7 | 101 | 65 | 22 | 865 | 0.6 |
| 8 | 461 | 455 | 84 | 3965 | 4.6 |

The Examples show that the heat of reaction is sufficient to separate the water of reaction by means of flash distillation. The flash distillation reduces the content of pentanal in the product to below 0.2% by weight, so that it can be processed further without additional fractionation.

The disclosure of priority German Application Number 19956410.8 filed Nov. 11, 1999 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A process for preparing α,β-unsaturated keto compounds by base-catalyzed aldol condensation of aldehydes and/or ketones having from 1 to 15 carbon atoms, comprising:
   reacting the aldehydes and/or ketones with an aqueous catalyst solution under adiabatic reaction conditions; and
   separating the reaction mixture obtained by rapid distillation into a top product comprising water, aldehyde and/or ketone and a bottom product comprising α,β-unsaturated keto compounds and aqueous catalyst phase;
   wherein a residence time of said reaction mixture in the rapid distillation stage is not more than one minute.

2. The process according to claim 1, wherein the top product is separated into an organic phase and an aqueous phase.

3. The process according to claim 2, wherein the organic phase of the top product is returned to the aldol condensation reaction.

4. The process according to claim 1, wherein the bottom product is separated into an organic phase and the aqueous catalyst phase.

5. The process according to claim 4, wherein the aqueous catalyst phase is returned to the aldol condensation reaction.

6. The process according to claim 1, wherein the aldol condensation is conducted at a pressure ranging from 1.1 to 20 bar.

7. The process according to claim 1, wherein the rapid distillation is a flash distillation, a distillation in a falling film evaporator, a distillation in a thin film evaporator or a distillation in a combined falling film/thin film evaporator.

8. The process according to claim 1, wherein the aldol condensation is conducted in at least one tube reactor.

9. The process according to claim 1, wherein the aldol condensation is conducted in at least one stirred vessel.

10. The process according to claim 1, wherein the aqueous catalyst solution is aqueous sodium hydroxide solution.

11. The process according to claim 1, wherein the α,β-unsaturated keto compounds have two hydrogen atoms on the α carbon atom and are selected from the group consisting of acetaldehyde, propanal, n-butyraldehyde, n-valeraldehyde, 3-methylbutyraldehyde, n-hexanal, 3-methylpentanal, 4-methylpentanal, n-heptanal, n-octanal, n-nonanal, n-decanal, acetone, methyl ethyl ketone, cyclohexanone and acetophenone.

12. The process according to claim 1, wherein, in the event at least two keto compounds are used in admixture as the reactant, at least one the α,β-unsaturated keto compounds has two hydrogen atoms on the α a carbon atom.

13. The process according to claim 12, wherein the mixture of keto compounds contains a keto compound having one hydrogen on an α carbon atom and is selected from the group consisting of isobutyraldehyde, 2-methylbutyraldehyde, 2-methylpentanal, 2-ethylhexanal, cyclohexyl carbaldehyde and phenyl-2-propyl ketone.

14. The process according to claim 1, wherein the aqueous catalyst solution contains base in a concentration ranging from 0.1 to 10% by weight.

15. The process according to claim 14, wherein the concentration of base in solution ranges from 0.1 to 3% by weight.

16. The process according to claim 1, wherein the weight ratio of α,β-unsaturated keto compounds to aqueous catalyst is at least 1:2.

17. The process according to claim 16, wherein the weight ratio of α,β-unsaturated keto compounds to aqueous catalyst is greater than 1:10.

18. The process according to claim 1, wherein a temperature of the bottom product during the rapid distillation is lower than the of a feed.

* * * * *